United States Patent [19]

Kawamura et al.

[11] Patent Number: 4,636,459
[45] Date of Patent: Jan. 13, 1987

[54] PHOTOPOLYMERIZABLE COMPOSITIONS

[75] Inventors: Kouichi Kawamura; Yoshimasa Aotani; Akira Umehara; Seiji Horie, all of Kanagawa, Japan

[73] Assignee: Fuji Photo Film Co., Ltd., Kanagawa, Japan

[21] Appl. No.: 836,942

[22] Filed: Mar. 6, 1986

[30] Foreign Application Priority Data

Mar. 6, 1985 [JP] Japan .................................. 60-44027
Mar. 6, 1985 [JP] Japan .................................. 60-44029
Mar. 7, 1985 [JP] Japan .................................. 60-45531
Mar. 7, 1985 [JP] Japan .................................. 60-45532

[51] Int. Cl.$^4$ .............................................. G03C 1/68
[52] U.S. Cl. ..................................... 430/288; 430/281; 430/919; 430/920; 430/924; 522/50; 522/63
[58] Field of Search ............... 430/919, 920, 281, 924, 430/288; 522/50, 63

[56] References Cited

U.S. PATENT DOCUMENTS 3,844,790 10/1974 Chang et al. ........................ 430/920
4,356,247 10/1982 Aotani et al. ...................... 430/920
4,459,349 7/1984 Tanaka et al. ..................... 430/920

Primary Examiner—Jack P. Brammer
Attorney, Agent, or Firm—Sughrue, Mion, Zinn, Macpeak and Seas

[57] ABSTRACT

A photopolymerizable composition containing an addition polymerizable compound having at least one ethylenically unsaturated double bond and a photopolymerization initiator is disclosed, wherein the photopolymerizable composition contains at least one compound represented by following general formula (I) or (II) as the photopolymerization initiator:

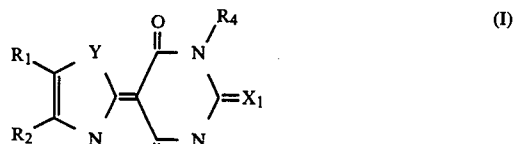

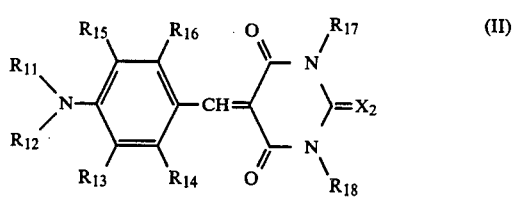

wherein, $R_1$, $R_2$, $R_3$, $R_4$, and $R_5$ each represents a hydrogen atom, an alkyl group, a substituted alkyl group, an aryl group, a substituted aryl group, an allyl group or a substituted allyl group, said $R_1$ and $R_2$ may combine with each other to form a ring together with the carbon atoms to which they are bonded; Y represents —O—, —S—, —Se—, —C(CH$_3$)$_2$— or —CH=CH—; $X_1$ represents an oxygen atom or a sulfur atom; $R_{11}$, $R_{12}$, $R_{17}$, and $R_{18}$ each represents a hydrogen atom, an alkyl group, a substituted alkyl group, an aryl group, a substituted aryl group, an allyl group, or a substituted allyl group; $R_{13}$, $R_{14}$, $R_{15}$, and $R_{16}$ each represents a hydrogen atom, an alkyl group, a substituted alkyl group, an aryl group, a substituted aryl group, a halogen atom, a carboalkoxy group, or an alkoxy group; said $R_{11}$ and $R_{15}$, said $R_{12}$ and $R_{13}$, said $R_{15}$ and $R_{16}$, and said $R_{13}$ and $R_{14}$ each may combine with each other to form a ring together with the carbon atoms to which they are bonded; and $X_2$ represents an oxygen atom or a sulfur atom.

10 Claims, No Drawings

PHOTOPOLYMERIZABLE COMPOSITIONS

FIELD OF THE INVENTION

This invention relates to a photopolymerizable composition. More specifically, the invention relates to a photopolymerizable composition composed of a polymerizable compound having an ethylenically unsaturated bond, a photopolymerization initiator, and, if necessary, a binder, and in particular, to a photopolymerizable composition useful for light-sensitive layers of light-sensitive printing plates, photoresists, etc.

BACKGROUND OF THE INVENTION

It is known to make copies of an image by a photographic means using a light-sensitive composition composed of a mixture of a polymerizable compound having an ethylenically unsaturated bond, a photopolymerization initiator, and further, if necessary, a suitable binder having a film-forming faculty and a thermal polymerization inhibitor. That is, as described in U.S. Pat. Nos. 2,927,022, 2,903,356, and 3,870,524, since this kind of light-sensitive composition can be hardened and insolubilized by the irradiation of light, a desired hardened image of a photopolymerizable composition can be formed by forming a proper layer or film using the light-sensitive composition, irradiating the layer or film by light through a negative of a desired image, and then removing only the unexposed portions with a proper solvent. The light-sensitive composition of this type is as a matter of course very useful for making light-sensitive printing plates, photoresists, etc.

Hitherto, since a polymerizable compound having an ethylenically unsaturated bond does not show a sufficient light sensitivity by itself only, it has been proposed to add thereto a photopolymerization initiator for increasing the light sensitivity thereof and as such a photopolymerization initiator, there are benzyl, benzoin, benzoin ethyl ether, Michler's ketone, anthraquinone, acridine, phenazine, benzophenone, 2-ethylanthraquinone, etc.

However, the use of such a photopolymerization initiator for a photopolymerizable composition encounters such problems that since the photopolymerizable composition has a low respondence for hardening and a long light exposure time is required for forming images, an image having good image quality is not reproduced even by the existence of slight vibration in operation in the case of reproducing precise images and also since the amount of energy of a light source for light exposure must be increased, it is required to take a counterplan to the dissipation of a large amount of heat generated by the increase of the light exposure energy and further the layer or film of the composition is liable to deform or change quality. Therefore, it has been desired to develop a photopolymerization initiator without having the above-described problems.

Also, these conventional photopolymerization initiators show very low photopolymerizing faculty for a light source of a visible light region of 400 nm or more as compared to the photopolymerizing faculty for a light source of a ultraviolet region of 400 nm or less in wavelength and accordingly the applicable range of the photopolymerizable compositions containing them is greatly limited or narrowed.

Hitherto, various attempts have been proposed in regard to a photopolymerization system responding visible light. For example, U.S. Pat. No. 2,850,445 describes that certain kinds of photoreducible dyes such as, for example, Rose Bengale, Eosine, erythrosine, etc., have an effective visible light respondence. Thereafter, as the improvements of the above-described techniques, there are proposed a polymerization initiation system composed of a dye and an amine (e.g., Japanese Patent Publication No. 20189/69, corresponding to British Pat. Nos. 1,135,280, 1,146,497 and 1,146,498), a system composed of a hexaarylbiimidazole, a radical generating agent, and a dye (e.g., Japanese Patent Publication No. 37377/70, corresponding to U.S. Pat. No. 3,479,185), a system composed of a hexaarylbiimidazole and a p-dialkylaminobenzylidene ketone (e.g., Japanese Patent Application (OPI) Nos. 2528/72, corresponding to U.S. Pat. No. 3,652,275, and 155292/79, corresponding to U.S. Pat. No. 4,162,162), and a system composed of a substituted triazine and a merocyanine dye (e.g., Japanese Patent Application (OPI) No. 151024/79). The term "OPI" as used herein refers to a "published unexamined Japanese patent application".

These effective may be effective for visible light, but the light-sensitive speed of these systems is not yet satisfactory and hence a further improvement has been desired.

SUMMARY OF THE INVENTION

A first object of this invention is, therefore, to provide a photopolymerizable composition having high light sensitivity.

A second object of this invention is to provide a photopolymerizable composition containing a general polymerizable compound having an ethylenically unsaturated bond and a photopolymerization initiator capable of increasing the photopolymerization speed of the photopolymerizable composition.

A third object of this invention is to provide a photopolymerizable composition having a high sensitivity or respondence for visible light 400 nm or more in wavelength, in particular, light of about 488 nm corresponding to the output of arogon laser.

As the result of various investigations for attaining the above-described objects of this invention, it has been discovered that specific photopolymerization initiation system have a function of greatly increasing the photopolymerization speed of polymerizable compounds having an ethylenically unsaturated bond and further some of these specific photopolymerization initiators also show high sensitivity for visible light having wavelength of 400 nm or more in addition to the above-described function, and have succeeded in achieving this invention based on the discoveries.

Thus, according to this invention, there is provided a photopolymerizable composition containing an addition polymerizable compound having at least one ethylenically unsaturated double bond and a photopolymerization initiator, wherein said composition contains at least one compound represented by following general formula (I) or (II) as the photopolymerization initiator.

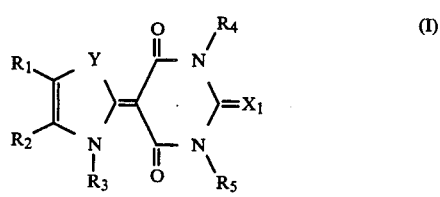

wherein, $R_1$, $R_2$, $R_3$, $R_4$, and $R_5$ each represents a hydrogen atom, an alkyl group, a substituted alkyl group, an aryl group, a substituted aryl group, an allyl group or a substituted allyl group; Y represents —O—, —S—, —Se—, —C(CH$_3$)$_2$— or —CH=CH—; and $X_1$ represents an oxygen atom or a sulfur atom; said $R_1$ and $R_2$ may combine with each other to form a ring together with carbon atoms to which they are bonded, and

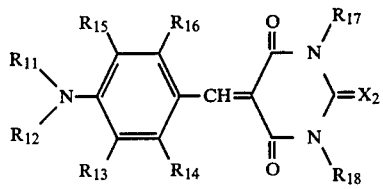

wherein $R_{11}$, $R_{12}$, $R_{17}$, and $R_{18}$ each represents a hydrogen atom, an alkyl group, a substituted alkyl group, an aryl group, a substituted aryl group, an allyl group, or a substituted allyl group; $R_{13}$, $R_{14}$, $R_{15}$, and $R_{16}$ each represents a hydrogen atom, an alkyl group, a substituted alkyl group, an aryl group, a substituted aryl group, a halogen atom, a carboalkoxy group, or an alkoxy group; said $R_{11}$ and $R_{15}$, said $R_{12}$ and $R_{13}$, said $R_{15}$ and $R_{16}$, or said $R_{13}$ and $R_{14}$ each may combine with each other to form a ring together with the carbon atoms to which they are bonded; and $X_2$ represents an oxygen atom or a sulfur atom.

The photopolymerizable composition of this invention may further contain, if necessary, a binder.

DESCRIPTION OF THE PREFERRED EMBODIMENT

Then, the invention is explained below in detail.

The polymerizable compound having ethylenically unsaturated bond in the photopolymerizable composition of this invention is a compound having at least one ethylenically unsaturated bond in the chemical structure and has a chemical form such as a monomer, a prepolymer (e.g., a dimer, a trimer, and other oligomers), a mixture thereof, and copolymers thereof. Examples of the polymerizable compound are unsaturated carboxylic acids, salts thereof, esters of unsaturated carboxylic acids and aliphatic polyhydric alcohols, amides of unsaturated carboxylic acids and aliphatic polyvalent amine compounds, etc.

Specific examples of the unsaturated carboxylic acid are acrylic acid, methacrylic acid, itaconic acid, crotonic acid, isocrotonic acid, maleic acid, etc.

Specific examples of the salt of unsaturated carboxylic acid are the sodium salts and potassium salts of the above-illustrated acids.

Specific examples of the ester of an aliphatic polyhydric alcohol compound and an unsaturated carboxylic acid are acrylic acid esters such as ethylene glycol diacrylate, triethylene glycol triacrylate, 1,3-butanediol diacrylate, tetramethylene glycol diacrylate, propylene glycol diacrylate, trimethylolpropane triacrylate, trimethylolethane triacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipenytaerythritol tetraacrylate, sorbitol triacrylate, sorbitol tetraacrylate, sorbitol pentaacrylate, sorbitol hexaacrylate, polyester acrylate oligomer, etc.; methacrylic acid esters such as tetramethylene glycol dimethacrylate, triethylene glycol dimethacrylate, trimethylolpropane trimethacrylate, trimethylolethane trimethacrylate, ethylene glycol dimethacrylate, 1,3-butanediol dimethacrylate, pentaerythritol dimethacrylate, pentaerythritol trimethacrylate, dipentaerythritol dimethacrylate, sorbitol trimethacrylate, sorbitol tetramethacrylate, bis[p-(3-methacryloxy-2-hydroxypropoxy)phenyl]dimethylmethane, bis-[p-(acryloxyethoxy)phenyl]dimethylethane, etc.; itaconic acid esters such as ethylene glycol diitaconate, propylene glycol diitaconate, 1,3-butanediol diitaconate, 1,4-butanediol diitaconate, tetramethylene glycol diitaconate, pentaerythritol diitaconate, sorbitol tetraitaconate, etc.; crotonic acid esters such as ethylene glycol dicrotonate, tetramethylene glycol dicrotonate, pentaerythritol dicrotonate, sorbitol tetracrotonate, etc.; isocrotonic acid esters such as ethylene glycol diisocrotonate, pentaerythritol diisocrotonate, sorbitol tetraisocrotonate, etc.; and maleic acid esters such as ethylene glycol dimaleate, triethylene glycol dimaleate, pentaerythritol dimaleate, sorbitol tetramaleate, etc.

Furthermore, mixture of the above-described esters may be used.

Specific examples of the amide of an aliphatic polyvalent amine and an unsaturated carboxylic acid are methylenebis-acrylamide, methylenebis-methacrylamide, 1,6-hexamethylenebis-acrylamide, 1,6-hexamethylenebis-methacrylamide, diethylenetriaminetrisacrylamide, xylylenebis-acrylamide, xylylenebis-methacrylamide, etc.

Examples of other polymerizable compound are the vinyl-urethane compounds having two or more polymerizable vinyl groups in one molecule prepared adding a vinyl monomer having the hydroxy group represented by following general formula (III) to a polyisocyanate compound having two or more isocyanate groups in one molecule described in Japanese Patent Publication No. 41708/73;

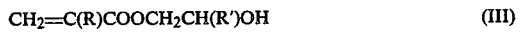

$$CH_2=C(R)COOCH_2CH(R')OH \qquad (III)$$

wherein R and R' each represents a hydrogen atom or a methyl group.

Then, the photopolymerization initiators which are the primary feature in the photopolymerizable compositions of this invention are explained below in detail.

One of the photopolymerization initiators for use in this invention is the merocyanine compound represented by general formula (I) described above.

In formula (I), $R_1$, $R_2$, $R_3$, $R_4$, and $R_5$, which may be the same or different, each represents a hydrogen atom, an alkyl group having 1 to 12 carbon atoms, such as a methyl group, an ethyl group, a n-propyl group, an i-propyl group, a n-butyl group, a t-butyl group, etc., an aryl group having 6 to 10 carbon atoms, such as a phenyl group, a naphthyl group, etc., or an allyl group. These alkyl group, aryl group, and allyl group each may have a substituent. Examples of the substituent are an alkyl group having 1 to 6 carbon atoms, such as a methyl group, an ethyl group, etc., an alkoxy group having 1 to 6 carbon atoms such as a methoxy group, an ethoxy group, etc., a halogen atom such as chlorine, bromine, etc., a cyano group, an amino group, an amino group substituted by an alkyl group of 1 to 4 carbon atoms, such as a dimethylamino group, etc., a carboalkoxy group having an alkyl group of 1 to 4 carbon atoms, such as a carbomethoxy group, etc., a substituted or unsubstituted aryl group having 6 to 10 carbon atoms, such as a phenyl group, p-methoxyphenyl group, a p-chlorophenyl group, etc., a carboxylic acid group, a sulfonic acid group, and the salt groups of these acids. $R_1$ and $R_2$ in formula (I) may be combined with each other to form a ring together with carbon atoms to which they are bonded and examples of the ring are an aliphatic hydrocarbon ring such as a cyclohexene ring, etc., aromatic rings such as a benzene ring, a naphthalene ring, etc., and heteroarocyclic rings such as a quinoline ring, etc. These rings may have a substituent as illustrated above in regard to the substituents for the groups shown by $R_1$ to $R_5$.

In general formula (I), Y represents a divalent atom selected from —O—, —S— and —Se— or an atomic group selected from —C(CH$_3$)$_2$— and —CH=CH— and $X_1$ represents an oxygen atom or a sulfur atom as described hereinbefore.

The merocyanine compound for use in this invention shown by general formula (I) described above can be prepared by known methods as described, for example, in T. H. James, *The Theory of Photographic Process*, 4th Ed., published by Macmillan Co., New York (1977) and F. M. Hamer, *The Cyanine Dyes and Related Compounds*, published by John Wiley & Sons Co., New York (1964). For example, as described above, the merocyanine compounds can be prepared from the compounds represented by following general formula (IV) and the compounds represented by following general formula (V):

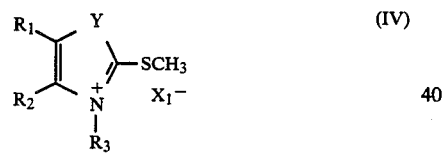
(IV)

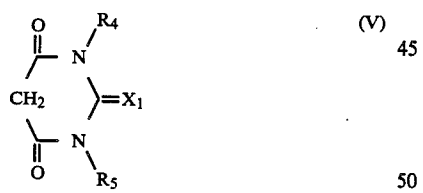
(V)

wherein $R_1$, $R_2$, $R_3$, $R_4$, $R_5$, $X_1$, and Y have the same signification as defined above about general formula (I).

Specific examples of the compound for use in this invention represented by general formula (I) described above are illustrated below although the invention is limited to these compounds.

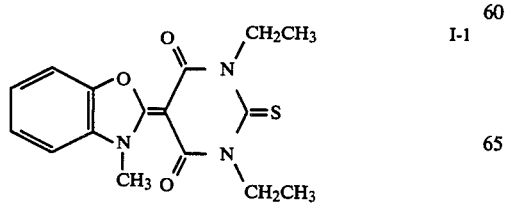
I-1

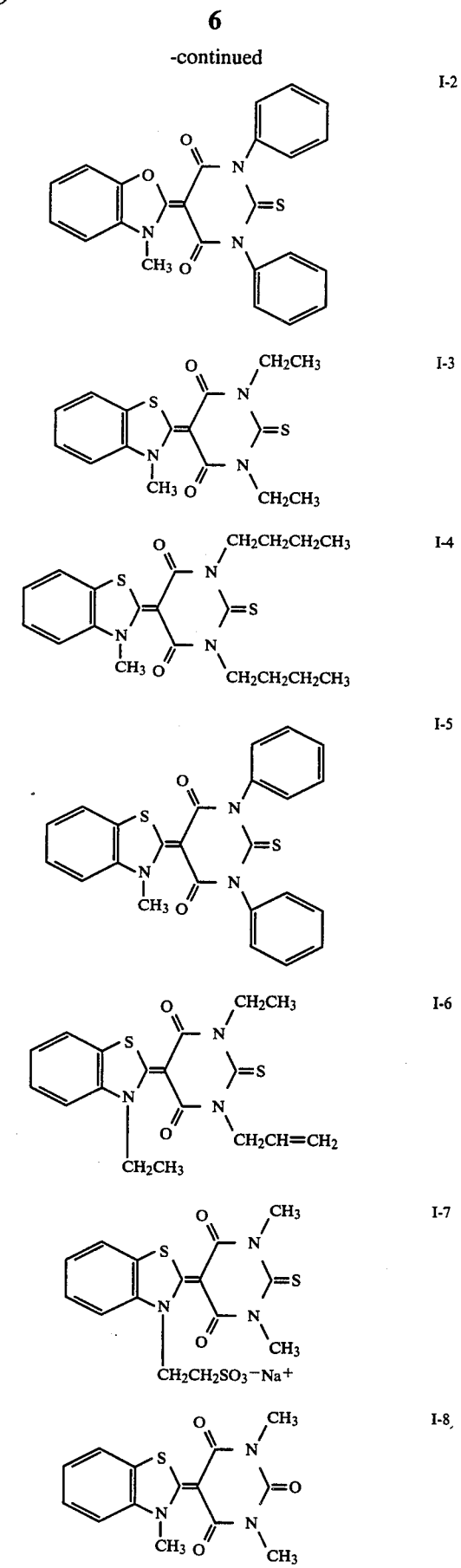

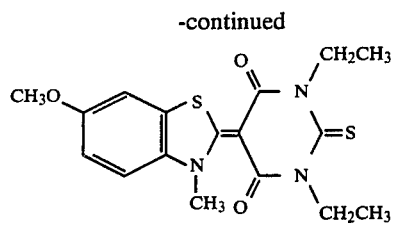
I-9
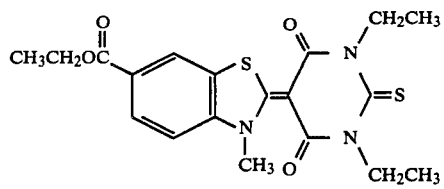
I-10
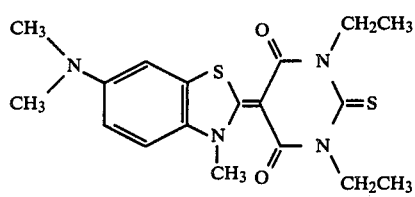
I-11
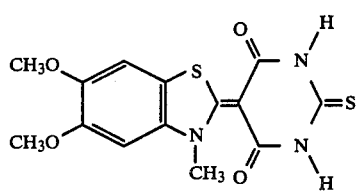
I-12
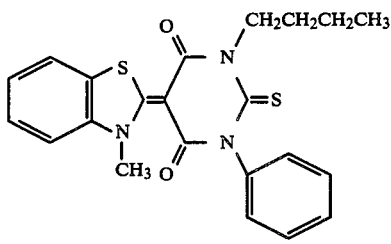
I-13
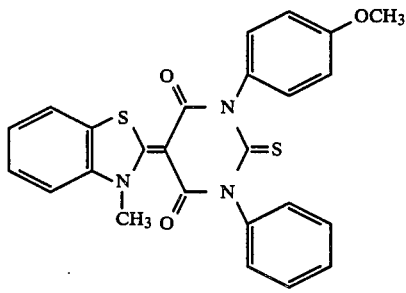
I-14
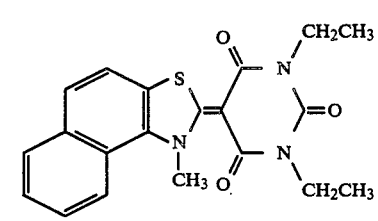
I-15
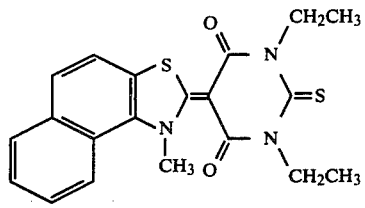
I-16
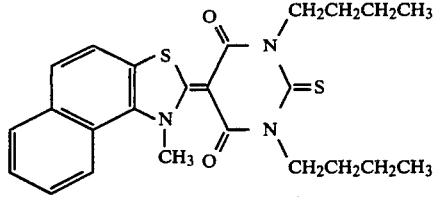
I-17
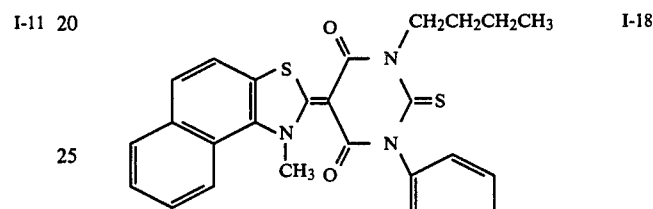
I-18
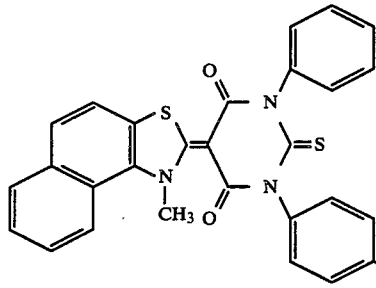
I-19
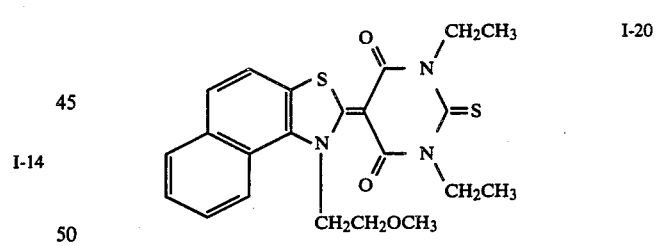
I-20
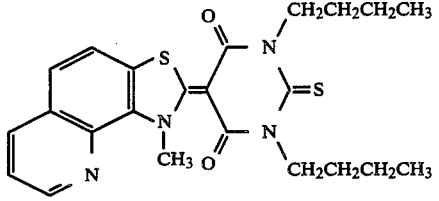
I-21
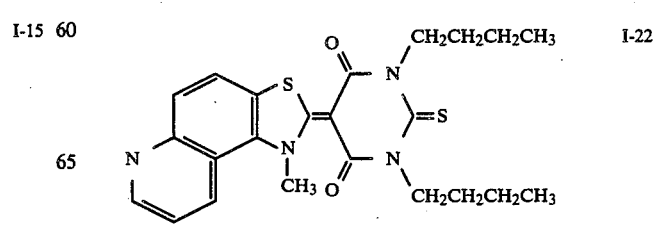
I-22

-continued

I-23 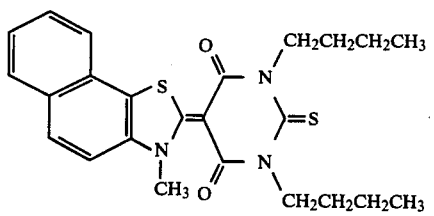

I-24 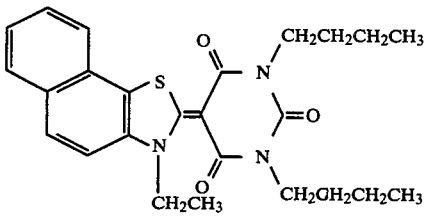

I-25 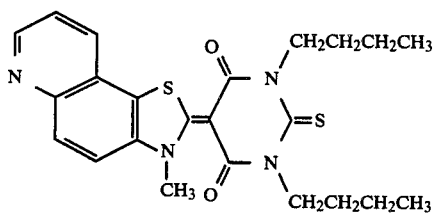

I-26 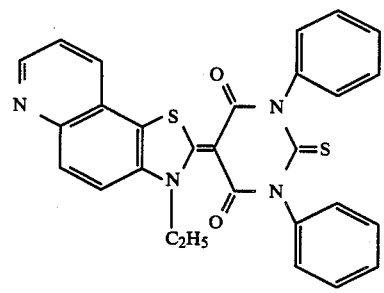

I-27 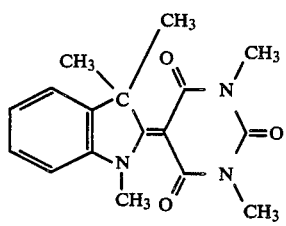

I-28 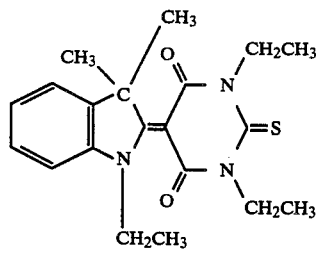

I-29 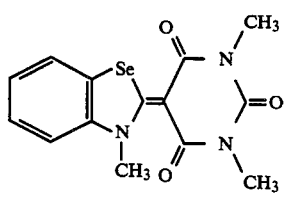

-continued

I-30 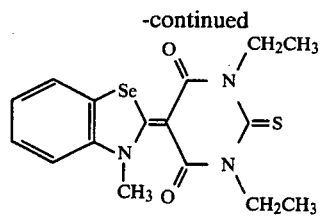

I-31 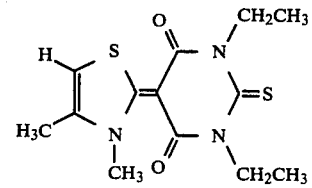

I-32 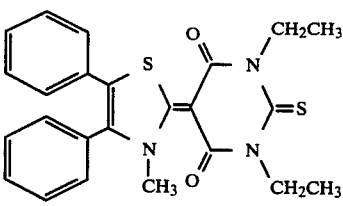

I-33 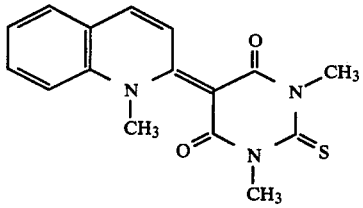

I-34 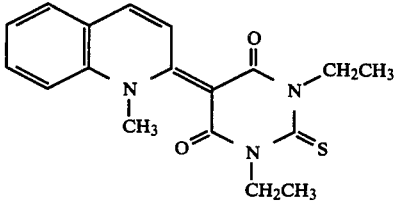

Other one of the polymerization initiators for use in this invention is the benzylidene compound represented by general formula (II) described above.

In formula (II), $R_{11}$, $R_{12}$, $R_{17}$, and $R_{18}$, which may be the same or different, each represents a hydrogen atom, an alkyl group having 1 to 12 carbon atoms, such as a methyl group, an ethyl group, a n-propyl group, an i-propyl group, a n-butyl group, a t-butyl group, etc., an aryl group having 6 to 10 carbon atoms, such as a phenyl group, a naphthyl group, etc., or an allyl group. These alkyl, aryl and allyl groups may have a substituent. Examples of the substituents are an alkyl group having 1 to 6 carbon atoms, such as a methyl group, an ethyl group, etc., an alkoxy group having 1 to 6 carbon atoms, such as methoxy group, an ethoxy group, etc., a halogen atom such as chlorine, bromine, etc., a cyano group, an amino group, an amino group substituted by an alkyl group of 1 to 4 carbon atoms, such as a dimethylamino group, etc., a carboalkyl group having an alkyl group of 1 to 4 carbon atoms, such as carbomethoxy group, a substituted or unsubstituted aryl group having 6 to 10 carbon atoms, such as a phenyl group, a p-methoxyphenyl group, a p-chlorophenyl group, etc., a carboxylic acid group, a sulfonic group, or the salts groups of these acids.

In formula (II), $R_{13}$, $R_{14}$, $R_{15}$, and $R_{16}$ each represents a hydrogen atom, a halogen atom such as chlorine, bromine, etc., a carboalkoxy group having 2 to 8 carbon atoms, such as a carbomethoxy group, a carboethoxy group, etc., an alkoxy group having 1 to 7 carbon atoms, such as a methoxy group, an ethoxy group, etc., or the alkyl group, substituted alkyl group, aryl group, or substituted aryl group as illustrated above as to $R_{11}$, $R_{12}$, $R_{17}$, and $R_{18}$.

Also, said $R_{11}$ and $R_{15}$, said $R_{12}$ and $R_{13}$, said $R_{15}$ and $R_{16}$, or said $R_{13}$ and $R_{14}$ may combine with each other together with the carbon atoms to which they are bonded to form a ring. Examples of the ring are an aliphatic hydrocarbon ring such as a cyclohexene ring, etc., a heterocyclic ring such as a morpholino ring, a duroridino ring, etc., an aromatic ring such as a benzene ring, a naphthalene ring, etc., and a heterocyclic ring such as a quinoline ring, etc. These rings may have a substituent as illustrated above in regard to the substituent for the groups shown by $R_{11}$, $R_{12}$, $R_{17}$, and $R_{18}$.

The polymerization initiator for use in this invention represented by general formula (II) described above attains the specific object of this invention described hereinbefore. That is, the initiator imparts a high sensitivity for light of wavelength of 400 nm or more, in particular for light of about 488 nm in wavelength corresponding to the output of argon laser to the photopolymerizable composition containing the initiator in addition to the function of increasing the photopolymerization speed of the composition. Thus, the use of the polymerization initiator shown by general formula (II) is suitable in the case of obtaining a photopolymerizable composition using argon laser as the light source for light exposure.

The polymerization initiator shown by general formula (II) can be synthesized by the compounds represented by following general formulae (VI) and (VII):

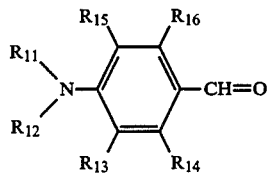
(VI)

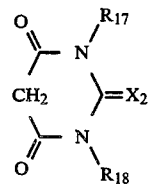
(VII)

wherein $R_{11}$, $R_{12}$, $R_{13}$, $R_{14}$, $R_{15}$, $R_{16}$, $R_{17}$, $R_{18}$, and $X_2$ have the same signification as defined above about general formula (II).

Then, specific examples of the benzylidene compound for use in this invention represented by general formula (II) are illustrated below.

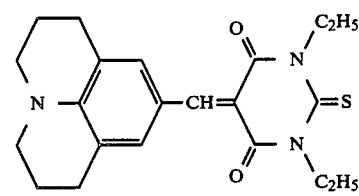
II-1

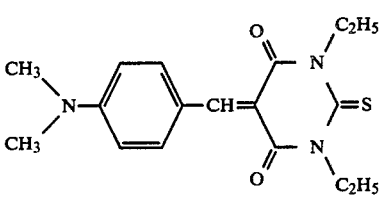
II-2

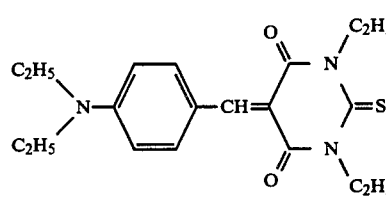
II-3

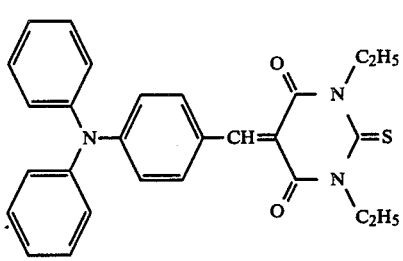
II-4

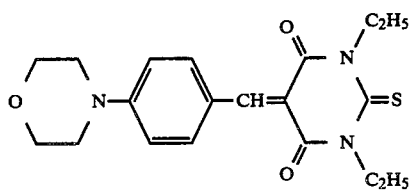
II-5

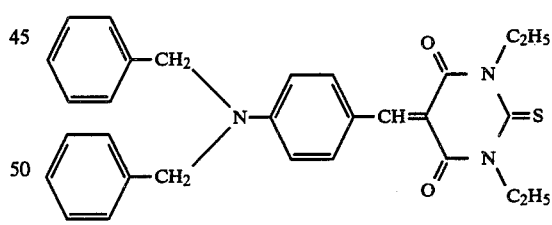
II-6

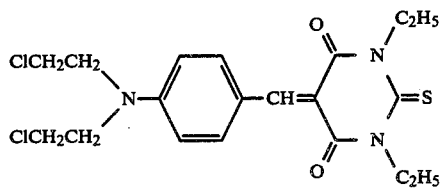
II-7

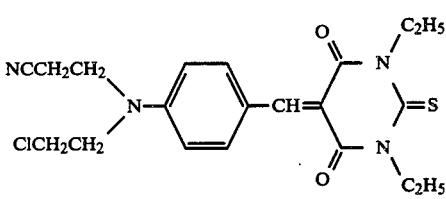
II-8

-continued
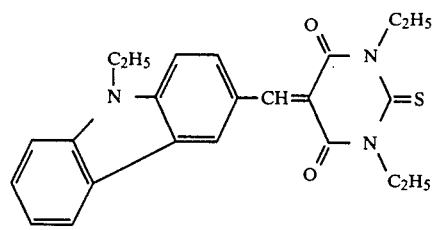
II-9
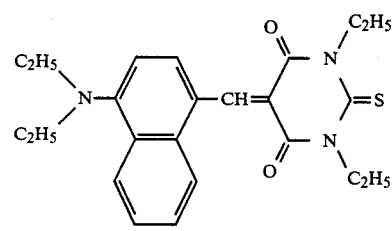
II-10
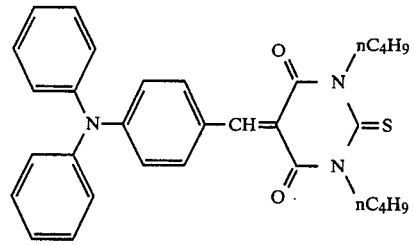
II-11
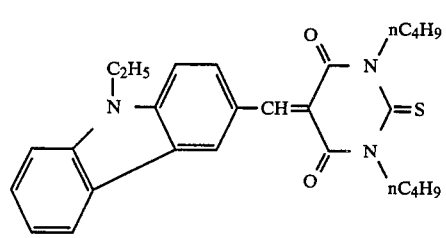
II-12
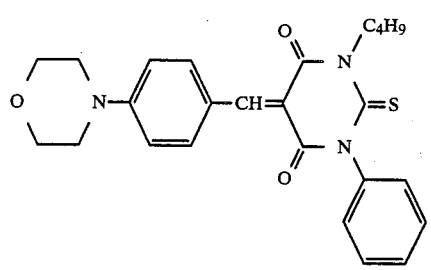
II-13
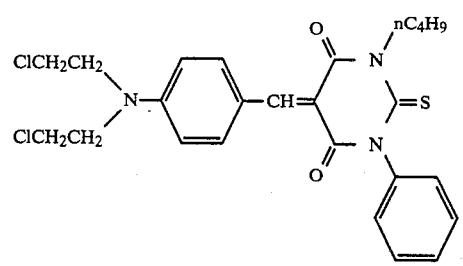
II-14
-continued
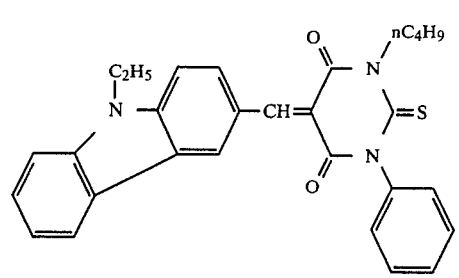
II-15
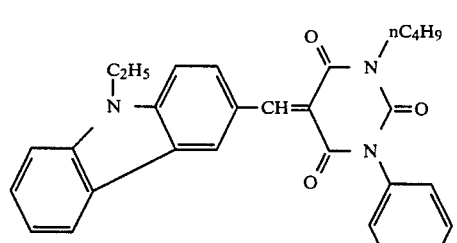
II-16
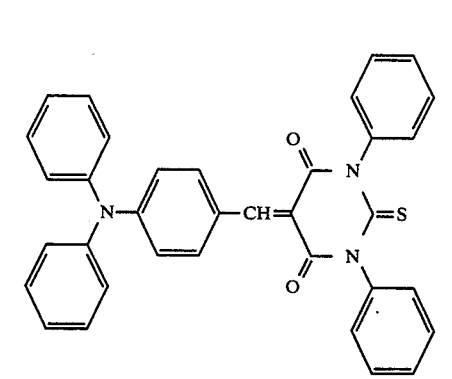
II-17
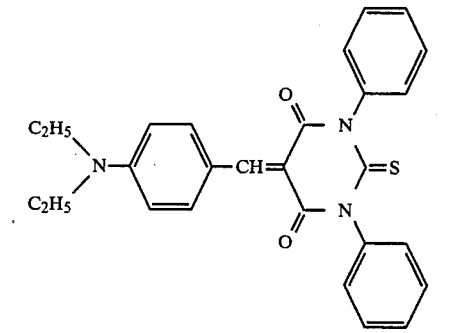
II-18
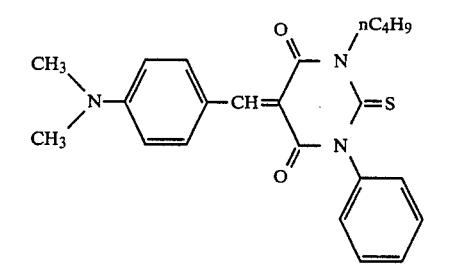
II-19

II-20

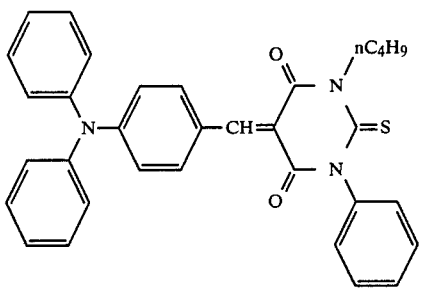

The polymerization initiator for use in this invention represented by above-described formula (I) or (II) can be generally used together with the following active agent showing a high polymerization initiating faculty.

(1) Carbonyl Compound:

There are benzyl, benzoin, benzylketals, benzoin ethers, etc.

An example of benzylketals is dimethoxy-2-phenylacetophenone and other examples thereof are described in Japanese Patent Application (OPI) Nos. 42653/74 and 99147/74, Japanese Patent Publication No. 29930/75 (corresponding to U.S. Pat. No. 3,801,329), etc.

Examples of benzoin ethers are o-methylbenzoin, o-ethylbenzin, etc., and other examples are described in Journal of American Chemical Society, Vol. 97, 1519 (1975).

Other examples of carbonyl compound which can be used in this invention together with the aforesaid polymerization initiator are acetophenone derivatives such as diethoxyacetophenone, etc., the compounds such as benzoyl-1-cyclohexanol, etc., described in European Pat. No. 125,206A1, the aroaliphatic ketones such as 2-morpholino-2-methyl-p-methylthiopropiophenone, etc., described in U.S. Pat. No. 4,318,791, and 2-hydroxyacetophenone derivatives such as 2-hydroxy-2-methyl-p-chloropropiophenone, etc.

(2) Sulfonyloxime Compound:

Examples of the compound are the sulfonyloxime compounds described in Japanese Patent Application (OPI) No. 53747/82, West German Patent Application (OLS) No. 3,410,387A1, and U.S. Pat. No. 4,258,121. Specific examples thereof are 2-phenyl-3-phenylsulfonyloxy-4-(3H)quinazolinone, 2-styryl-3-phenylsulfonyloxy-4(3H)quinazolinone, N-hydroxy-1,8-naphthalimidobenzenesulfonic acid ester, etc.

(3) Acyloxime Compound:

Examples of the compound are 1-phenyl-1,2-propanedione-2-(o-ethoxycarbooxime), etc., as well as the compounds described in Progress in Organic Coatings, Vol. 3, 115 (1975).

(4) Hexaarylbiimidazole Compound:

Specific examples of preferred hexaarylbiimidazole are 2,2'-bis(o-chlorophenyl)-4,4', 5,5'-tetraphenylbiimidazole, 2,2'-bis(o,p-dichlorophenyl)-4,4',5,5'-tetraphenylbiimidazole, etc. Other examples thereof are described in Japanese Patent Publication No. 37377/70 (corresponding to U.S. Pat. No. 3,479,185).

(5) Halogenated Compound:

Examples of halogenated compounds which can be used in this invention are described in British Pat. Nos. 1,234,648, 2,039,073B, U.S. Pat. Nos. 3,827,596, 3,905,813, Japanese Patent Application (OPI) Nos. 24113/80 (corresponding to U.S. Pat. No. 4,212,970) and 15503/83.

Other examples thereof are described in British Pat. Nos. 1,388,492 and 1,602,903, German Pat. No. 3,337,024A1, and Bulletin of the Chemical Society of Japan, Vol. 42, 2924–2930 (1969).

Specific examples thereof are 2,6-di(trichloromethyl)-4-(p-methoxyphenyl)-1,3,5-triazine, 2,4,6-tri(trichloromethyl)-1,3,5-triazine, 2-trichloromethyl-5-(p-methoxystyryl)-1,3,4-oxadiazole, anthraquinone-1-sulfonyl chloride, 2,2,2-trichloroacetophenone, etc.

(6) Amino Compound:

Examples of amino compounds which can be used in this invention are described in M. R. Sander, et al., Journal of Polymer Society, Vol. 10, 3173 (1972), Japanese Patent Application (OPI) Nos. 82102/76 and 134692/77.

Specific examples thereof are trimethylamine, triethanolamine, p-dimethylaminobenzoic acid ethyl ester, p-cyanodimethylaniline, p-formyldimethylaniline, etc.

Other amino compounds include p-amino-substituted benzophenone derivatives and p-amino-substituted chalcone derivatives and specific examples thereof are Michler's ketone, p-dimethylaminobenzilideneacetophenone, 4,4'-dimethylaminochalcone, etc.

(7) Amino Acid:

A specific example of particularly preferred amino acid for use in this invention is N-phenylglycine.

(8) Sulfur Compound:

Examples of sulfur compound for use in this invention are described in U.S. Pat. Nos. 2,460,105 and 2,773,822. Specific examples thereof are dibenzothiazoyl disulfide, diethylxanthogen disulfide, 2-mercaptobenzothiazole, 2-mercaptobenzimidazole, 5-methylthio-2-mercaptothiadiazole, etc.

(9) Peroxide:

Specific examples of peroxides for use in this invention are dibenzoyl peroxide, 3,3',4,4'-tetra(t-butylperoxycarbonyl)benzophenone, etc.

Thus, the light sensitive of the photopolymerizable composition of this invention can be further increased by using the polymerizable initiator shown by formula (I) or (II) described above together with the active agent described above, in particular the carbonyl compound, the sulfonyloxime compound, the acyloxime compound, the halogenated compound or the hexaarylbiimidazole compound in the aforesaid compounds.

Moreover, the inventors have further proceeded investigations for far more increasing the light sensitivity of the photopolymerizable compositions of this invention and as the result thereof, it has further been discovered that the sensitivity of the photopolymerizable composition can be greatly improved by using the photopolymerization initiator represented by general formula (I) or (II) described above together with a combination of specific active agents, i.e., one of the component group (a) and one of the component group (b) described below.

That is, in a preferred embodiment of this invention, the photopolymerizable composition contains the polymerization initiator represented by general formula (I) or (II) described above together with at least one of the component group (a) consisting of a hexaarylbiimidazole and a sulfonyloxime compound represented by general formula (VIII)

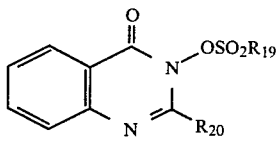

(VIII)

wherein $R_{19}$ and $R_{20}$ each represents an alkyl group, substituted alkyl group, an aryl group, a substituted aryl group, an alkenyl group, or a substituted alkenyl group, and at least one of the component group (b) consisting of an α,β-dicarbonyl compound, an N-phenylglycine, and a thiol compound represented by general formula (IX)

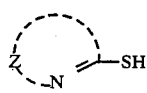

(IX)

wherein Z represents a non-metallic group necessary for forming a heterocyclic ring.

Some of the compounds belonging to the groups (a) and (b) were already described above as active compounds.

The hexaarylbiimidazole for use in this invention as the component group (a) in the preferred embodiment of the invention is a compound, which is called as a 2,4,5-triacrylimidazolyl dimer, having a structure wherein two imidazoles are bonded together with one covalent bond. As the aryl group for the hexaarylbiimidazole, a phenyl group is preferred. Such a phenyl group may have a substituent and a hexaphenylbiimidazole in which the ortho position of each of the phenyl groups at the 2-position and 2'-position thereof is substituted by a fluorine atom, a chlorine atom, a bromine atom, a nitro group, or a methyl group is particularly advantageous from the heat stability and the light reaction rate.

Specific examples of the particularly preferred hexaarylbiimidazole are 2,2'-bis(o-chlorophenyl)-4,4',5,5'-tetraphenylbiimidazole, 2,2'-bis(o-bromophenyl)-4,4',5,5'-tetraphenylbiimidazole, 2,2'-bis(o,p-dichlorophenyl)-4,4',5,5'-tetraphenylbiimidazole, 2,2'-bis(o-chlorophenyl)-4,4',5,5'-tetra(m-methoxyphenyl)-biimidazole, 2,2'-bis(o,o'-dichlorophenyl)-4,4',5,5'-tetraphenylbiimidazole, etc.

These hexaarylbiimidazoles can be easily prepared by the methods disclosed, for example, in *Bulletin of the Chemical Society of Japan*, 33, 565 (1960) and *Journal of Organic Chemistry*, 36, [16], 2262 (1971).

Another component for use in this invention as component group (a) is the sulfonyloxime compound represented by general formula (VIII) described above. In formula (VIII), $R_{19}$ and $R_{20}$, which may be the same or different, each represents an alkyl group having 1 to 12 carbon atoms, such as a methyl group, an ethyl group, etc., an aryl group having 6 to 10 carbon atoms, such as a phenyl group, a naphthyl group, etc., or an alkenyl group having 2 to 15 carbon atoms. These alkyl, aryl and alkenyl groups each may have a substituent. Examples of the substituent are an alkyl group having 1 to 6 carbon atoms, such as a methyl group, an ethyl group, etc. an alkoxy group having 1 to 6 carbon atoms, such as a methoxy group, an ethoxy group, etc., a halogen atom such as chlorine, bromine, etc., a cyano group, an amino group, an amino group substituted by an alkyl group of 1 to 4 carbon atoms, such as a dimethylamino group, etc., a carboalkoxy group having an alkyl group of 1 to 4 carbon atoms, such as a carbomethoxy group, etc., and a substituted or unsubstituted aryl group having 6 to 20 carbon atoms, such as a phenyl group, a p-methoxyphenyl group, a p-chlorophenyl group, an o,p-dichlorophenyl group, a p-tolyl group, a p-butylphenyl group, etc.

Preferred examples of $R_{19}$ are an aryl group such as a phenyl group or a substituted aryl group and preferred examples of $R_{20}$ are an aryl group such as a phenyl group or a substituted aryl group and an alkenyl group such as styryl group and a substituted alkenyl group.

Other preferred examples of the sulfonyloxime compound represented by general formula (VIII) and synthesis method of the sulfonyloxime compounds are described in Japanese Patent Application (OPI) Nos. 53747/82 and 174831/84, and West German Patent Application (OLS) No. 3,410,387A1.

The compound for use in this invention as one of the component group (b) described above is an α,β-dicarbonyl compound, an N-phenylglycine, or a thiol compound represented by general formula (IX) described above.

Specific examples of the α,β-dicarbonyl compound are barbituric acids such as N,N-dimethylbarbituric acid, N,N-diethylthiobarbituric acid, N,N-di-n-butylthiobarbituric acid, etc., alicyclic compounds such as dimedone, etc.

In the thiol compound shown by general formula (IX) described above, Z represents a non-metallic group necessary for forming a heterocyclic group such as thiazole, oxazole, imidazole, benzothiazole, benzimidazole, naphthothiazole, naphthoimidazole, oxadiazole, thiadiazole, triazole, tetrazole, pyrimidine, etc. Also, these heterocyclic rings may have a substituent and examples of the substituent are an alkyl group having 1 to 6 carbon atoms, such as a methyl group, an ethyl group, etc., an alkoxy group having 1 to 6 carbon atoms, such as a methoxy group, an ethoxy group, etc., a halogen atom such as chlorine, bromine, a cyano group, an amino group, an amino group substituted by an alkyl group of 1 to 4 carbon atoms, such as a dimethylamino group, etc., a carboalkoxy group having an alkyl group of 1 to 4 carbon atoms, such as a carbomethoxy group, etc., an aryl group having 6 to 20 carbon atoms, such as a phenyl group, a p-methoxyphenyl group, etc.

Also, the above-described heterocyclic ring may be condensed with an aromatic ring such as a benzene ring, a naphthalene ring, etc.

Specific examples of the thiol compound shown by general formula (IX) are 2-mercaptobenzothiazole, 2-mercaptobenzimidazole, 2-mercaptobenzoxazole, 2-mercapto-5-methylthiadiazole, 2-mercapto-5-methylthiothiadiazole, 2-mercapto-1-N-phenyl-1,3,4-triazole, etc.

The photopolymerizable composition of this invention may further contain, if necessary, a binder. The binder for use in this invention is required to have the properties that the binder has good compatibility with the polymerizable compound having an ethylenically unsaturated bond and the photopolymerization initiator(s) for use in this invention to an extent of not causing demixing in the whole steps of producing light-sensitive materials from the preparation of a coating solution containing the photopolymerizable composition to coating and drying it. The light-sensitive layer or the sist layer formed using the composition containing the binder can be developed after image exposure by solution development or peel off development, and also the composition containing the binder can form a tough film as a light-sensitive layer or a resist layer. The binder is usually selected from linear organic polymers.

Specific examples of the binder include chlorinated polyethylene, chlorinated polypropylene, polyacrylic acid alkyl esters (examples of the alkyl group are a methyl group, an ethyl group, a n-butyl group, an iso-butyl group, an n-hexyl group, a 2-ethylhexyl group, etc.), a copolymer of an acrylic acid alkyl ester (examples of the alkyl group are as illustrated above) and at least one monomer selected from acrylonitrile. vinyl chloride, vinylidene chloride, styrene, butadiene, etc., polyvinyl chloride, a copolymer of vinyl chloride and acrylonitrile, polyvinylidene chloride, a copolymer of vinylidene chloride and acrylonitrile, polyvinyl acetate, polyvinyl alcohol, polyacrylonitrile, a copolymer of acrylonitrile and styrene, a copolymer of acrylonitrile, butadiene, and styrene, a polymethacrylic acid alkyl ester (examples of the alkyl group are a methyl group, an ethyl group, a n-propyl group, a n-butyl group, an iso-butyl group, a n-hexyl group, a cyclohexyl group, a 2-ethylhexyl group, etc.), a copolymer of a methacrylic acid alkyl ester (examples of the alkyl group are as illustrated above) and at least one of the monomers such as acrylonitrile, vinyl chloride, vinylidene chloride, styrene, butadiene, etc., polystyrene, poly-α-methylstyrene, polyamide (6-nylon, 6,6-nylon, etc.), methyl cellulose, ethyl cellulose, acetyl cellulose, polyvinyl formal, polyvinyl butyral, etc.

Furthermore, when an organic high molecular polymer soluble in water or an aqueous alkali solution is used as the binder, the layer formed by the photopolymerizable composition containing the binder can be developed with water or an aqueous alkali solution. Examples of such a high molecular polymer are addition polymers having carboxylic acid at the side chain, such as methacrylic acid copolymers (e.g., a copolymer of methyl methacrylate and methacrylic acid, a copolymer of ethyl methacrylate and methacrylic acid, a copolymer of butyl methacrylate and methacrylic acid, a copolymer of benzyl methacrylate and methacrylic acid, a copolymer of ethyl acrylate and methacrylic acid, a copolymer of methacrylic acid, styrene, and methacrylic acid, etc.), acrylic acid copolymers (e.g., a copolymer of ethyl acrylate and acrylic acid, a copolymer of butyl acrylate and acrylic acid, a copolymer of ethyl acrylate, styrene, and acrylic acid, etc.), itaconic acid copolymers, crotonic acid copolymers, partially esterified maleic acid copolymers, etc., and also acid cellulose derivatives having carboxylic acid at the side chain.

These high molecular polymers may be used solely as the binder and may be used as a mixture of the high molecular polymers having good compatibility to an extent of not causing demixing in the steps of producing light-sensitive materials for the preparation of the coating solution of the composition to coating and drying at a proper mixing ratio.

The molecular weight of the high molecular polymer which is used as a binder in this invention may be in a wide range but in general 5,000 to 2,000,000, preferably 10,000 to 1,000,000.

Furthermore, it is preferred that the polymerizable composition of this invention contains a thermal polymerization inhibitor for preventing the occurrence of unnecessary thermal polymerization of the polymerizable compound having an ethylenically unsaturated bond in the composition during the production or storage of the composition. Examples of the proper thermal polymerization inhibitor are hydroquinone, p-methoxyphenol, di-t-butyl-p-cresol, pyrogallol, t-butyl catechol, benzoquinone, cuprous cloride, phenothiazine, chroranil, naphthylamine, β-naphthol, nitrobenzene, dinitrobenzene, etc.

Also, as the case may be, the polymerizable compositions of this invention may further contain dyes or pigments such as Methylene Blue, Crystal Violet, Rhodamine B, Fuchsine, Auramine, azoic dyes, anthraquinone series dyes, titanium oxide, carbon black, iron oxide, phthalocyanine pigments, azoic pigments, etc.

Furthermore, the photopolymerizable compositions of this invention may, if necessary, contain plasticizers. Examples of the plasticizers are phthalic acid esters such as dimethyl phthalate, diethyl phthalate, dibutyl phthalate, dihexyl phthalate, dicyclohexyl phthalate, ditridecyl phthalate, etc.; glycol esters such as dimethyl glycol phthalate, ethylphthalylethyl glycol, butylphthalylbutyl glycol, etc.; phosphoric acid esters such as tricresyl phosphate, triphenyl phosphate, etc.; and aliphatic dibasic acid esters such as diisobutyl adipate, dioctyl adipate, dibutyl sebacate, dibutyl maleate, etc.

The photopolymerizable composition of this invention described above is used by, for example, the following manner. That is, the above-described components constituting the composition are dissolved in a solvent and coated on a proper support by a conventional method as, for example, a light-sensitive layer of a light-sensitive printing plate or a photoresist layer.

In this case, preferred mixing ratios of the components for constituting the polymerizable composition of this invention in an embodiment of using the photopolymerization initiator of formula (I) or (II) described above together with the active agent showing a high photopolymerization initiating faculty described hereinbefore is 0.01 to 50 parts by weight, particularly 0.1 to 10 parts by weight of the photopolymerizable initiator, 0 to 1,000 parts by weight, particularly 0 to 500 parts by weight of a binder, 0 to 100 parts by weight, particularly 0 to 20 parts by weight of the active agent, 0 to 10 parts by weight, particularly 0 to 5 parts by weight of a thermal polymerization inhibitor, 0 to 50 parts by weight, particularly 0 to 20 parts by weight of a dye or pigment, and 0 to 200 parts by weight, particularly 0 to 50 parts by weight of a plasticizer per 100 parts by weight of a polymerizable compound having an ethylenically unsaturated bond.

Also, the mixing ratios of the components in a preferred embodiment of this invention using the photopolymerization initiator shown by formula (I) or (II) together with a combination of one of the component group (a) and one of the component group (b) described hereinbefore are 0.01 to 50 parts by weight, particularly 0.1 to 10 parts by weight of the photopolymerizable initiator, 0.01 to 50 parts by weight, particularly 0.1 to 10 parts by weight of component (a), 0.01 to 50 parts by weight, particularly 0.1 to 10 parts by weight of component (b), 0 to 1,000 parts by weight, particularly 0 to 500 parts by weight of a binder, 0 to 10 parts by weight, particularly 0 to 5 parts by weight of a thermal polymerization inhibitor, 0 to 50 parts by weight, particularly 0 to 20 parts by weight of a dye or pigment, and 0 to 200 parts by weight, particularly 0 to 50 parts by weight of a plasticizer per 100 parts by weight of a polymerizable compound having an ethylenically unsaturated bond.

As the solvent which is used in the case of coating the photopolymerizable composition of this invention, there are ethylene dichloride, cyclohexanone, methyl ethyl ketone, methylcellosolve, ethylcellosolve, methylcellosolve acetate, monochlorobenzene, toluene, xylene, ethyl acetate, butyl acetate, etc. These solvents may be used solely or as a mixture thereof.

In the case of producing a light-sensitive lithographic printing plate, the coating amount of the photopolymerizable composition of this invention is preferably 0.1 to 10.0 g/m$^2$, more preferably 0.5 to 5.0 g/m$^2$ as a solid.

The photopolymerizable composition of this invention is suitable for the light-sensitive layer of a light-sensitive lithographic printing material. In this case, as a support suitable for the light-sensitive lithographic printing plate, there are an aluminum plate subjected to hydrophilic treatment, such as a silicate-treated aluminum plate, an anodically oxidized aluminum plate, a silicate-electrodeposited aluminum plate, etc. Other examples of the support are a zinc plate, a stainless steel plate, a chrome-treated copper plate, a plastic plate or paper subjected to hydrophilic treatment, etc.

Also, the photopolymerizable composition of this invention can be used as photoresist and in this case, a copper plate, a copper-plated plate, a stainless plate, a glass plate, etc., can be used as the support.

Then, the following examples are intended to illustrate this invention but not to limit in any way.

First, synthesis examples of the photopolymerization initiators for use in this invention represented by general formulae (I) and (II) described above are shown.

SYNTHESIS EXAMPLE 1

Synthesis of Compound I-17 (Formula (I))

In 500 ml of acetonitrile were dissolved 35.4 g of N-methyl-2-methylmercaptobenzo[4,5]benzothiazolium tosylate and 21.7 g of 1,3-di-n-butylthiobarbituric acid and then 40 ml of triethylamine was added to the solution. After refluxing the mixture for 2 hours, the mixture was allowed to cool and crystals thus deposited were collected by filtration and recrystallized twice each with ethyl acetate to provide 31.0 g of crystals having melting point of 180° to 182° C.

Electron spectrum (in tetrahydrofuran [THF]): λmax: 399 nm; (log ε=4.72).

| Elemental Analysis for $C_{24}H_{27}O_2N_3S_2$: | | | |
|---|---|---|---|
| | C | H | N |
| Calculated: | 63.55% | 6.00% | 9.26% |
| Found: | 63.46% | 6.14% | 8.89% |

SYNTHESIS EXAMPLE 2

Synthesis of Compound II-19 (Formula (2))

In 5 liters of methanol were refluxed 37 g of p-dimethylaminobenzaldehyde and 69 g of N-n-butyl-N'-phenylthibarbituric acid for 2 hours. After allowing to cool the reaction mixture thus formed, crystals deposited were collected by filtration, dried, and recrystallized from a mixture of methanol and benzene to provide 32 g of crystals having melting point of 259.5° to 260.5° C.

Electron spectrum (in tetrahydrofuran [THF]): λmax: 487 nm; (log ε=4.85)

| Elemental Analysis for $C_{23}H_{25}N_3O_2S$: | | | |
|---|---|---|---|
| | C | H | N |
| Calculated: | 67.79% | 6.18% | 10.31% |
| Found: | 68.02% | 6.06% | 10.31% |

EXAMPLES 1 TO 3 AND COMPARISON EXAMPLES 1 TO 9

On an aluminum plate grained by a nylon brush and then subjected to a silicate treatment was coated the light-sensitive coating composition shown below using each of the photopolymerization initiators shown in Table 1 described below by means of a rotary coating device at a rotation speed of 200 rpm and dried for 5 minutes at 100° C. to form a light-sensitive layer of about 2 μm in dry thickness and thus to provide a light-sensitve plate.

Coating Composition:

Copolymer of benzyl methacrylate and methacrylic acid (73/27 in mole ratio): 5.0 g Pentaerythritol tetraacrylate: 3.6 g Photopolymerization initiator shown in Table 1 (1 mole% to monomer, i.e., the pentaerythritol tetraacrylate):

Methyl ethyl ketone: 20 g

Methylcellosolve acetate: 20 g

A step wedge (density different: 0.15, density step number: 15 steps) was placed on the light-sensitive plate thus obtained using a vacuum frame and the light-sensitive plate was exposed to a super high pressure mercury lamp of 2 KW for 7 seconds. After exposure, the light-sensitive plate was exposed using the developer having the following composition.

Developer:

Sodium tertiary phosphate: 25 g

Sodium primary phosphate: 5 g

Butylcellusolve: 70 g

Surface active agent: 2 ml

Water: 1 liter

The mixture step number of the step wedge corresponding to the appeared image is shown in Table 1 as the sensitivity of the light-sensitive material, wherein a higher step number means a higher sensitivity.

TABLE 1

| Example | Photopolymerization Initiator | Maximum Step No. of Step Wedge |
|---|---|---|
| 1 | I-16 | 10 |
| 2 | I-17 | 9 |
| 3 | I-18 | 11 |

For comparison, comparison light-sensitive plates were prepared by following the same procedure as described above using comparison compounds shown in Table 2 below as the photopolymerization initiator in place of the compound of this invention shown in Table 1 above in an amount of 1 mole% for each monomer, i.e., pentaerythritol tetraacrylate, and the sensitivity of each sample is also shown in Table 2.

TABLE 2

| Comparison Example | Photopolymerization inhibitor | Maximum Step No. of Step Wedge |
|---|---|---|
| 1 | (naphthothiazole-N-CH₃ structure with =C(C(O)N(C₂H₅)-C(=S)S-) substituent) | 0 |
| 2 | (naphthothiazole-N-CH₃ structure with =C(C(O)N(nC₆H₁₃)-S-C(=S)-) substituent) | 0 |
| 3 | (naphthothiazole-N-CH₃ structure with =C(C(O)N(nC₆H₁₃)-O-C(=S)-) substituent) | 0 |
| 4 | (naphthothiazole-N-CH₃ with =C(C(O)C₆H₅)₂ dibenzoylmethylene) | 2 |
| 5 | (naphthothiazole-N-CH₃ with indandione-1,3 ylidene) | 3 |
| 6 | (naphthothiazole-N-CH₃ with =CH-C(O)C₆H₅) | 7 |
| 7 | (naphthothiazole-N-CH₃ with =C(CN)C(O)OC₂H₅) | 3 |
| 8 | (naphthothiazole-N-CH₃ with isoxazole-phenyl ring system) | 0 |
| 9 | (naphthothiazole-N-CH₃ with 1,2-diphenylpyrazolidine-3,5-dione) | 3 |

As shown in Table 1 and Table 2 above, the light-sensitive plates using the photopolymerization initiators for use in this invention shown by formula (I) above show high sensitivity as compared with the samples in Comparison Examples 1 to 9, which sufficiently show the desired effect of this invention.

EXAMPLES 4 TO 6 AND COMPARISON EXAMPLE 10

By following the same procedure as in Examples 1 to 3 described above except that Compound I-17 shown by formula (I) above was used in an amount of 5 mole% to each monomer as the photopolymerization initiator and each of the compounds shown in Table 3 below was used in an amount of 5% to monomer as the active agent, each light-sensitive coating composition was prepared, each light-sensitive plate was prepared using the coating composition by the same manner as in Examples 1 to 3, and the light-sensitive plate was exposed by the same manner as Examples 1 to 3 except that the exposure time was 4 second, and then exposed as in the above examples. The maximum step number of the step wedge corresponding to the appeared image is shown in Table 3 as the sensitivity of the light-sensitive plate. Also, the sensitivity of a sample of Comparison Example 10 prepared by the same manner as above without using the active agent is shown in the same table. (Note: Comparison Example 10 is shown as "comparison" for the sample containing the active agent together with the photopolymerization initiator shown by formula (I) and is also an example of this invention since it contains the photopolymerization initiator shown by formula (I).

TABLE 3

| Example No. | Active Agent | Maximum Step No. of Step Wedge |
|---|---|---|
| Example 4 | 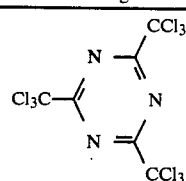 | 8 |
| Example 5 | 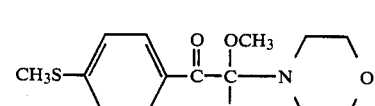 | 9 |
| Example 6 | 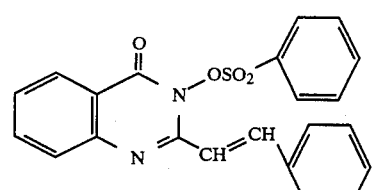 | 12 |
| Comparison Example 10 | None | 7 |

From the results shown in Table 3, it can be seen that by using the photopolymerization initiator of this invention shown by formula (I) above together with the active agent, the sensitivity of the light-sensitive material is clearly increased as compared with the case of using the photopolymerization initiator alone.

EXAMPLES 7 TO 10 AND COMPARISON EXAMPLES 11 TO 20

By following the same procedure as Examples 1 to 3 except that each of Compounds I-3, I-4, I-7 and I-13 shown by general formula (I) was used in an amount of 1 mole% to monomer as the photopolymerization initiator of this invention and 2-styryl-3-phenylsulfonyloxy-4(3H)quinazolinone was used in an amount of 5 mole% to monomer as the active agent, each light-sensitive plate was prepared and exposed and developed as in Examples 1 to 3. The maximum step number of the step wedge corresponding to the appeared image is shown in Table 4 as the sensitivity. Also, comparison samples were prepared by following the same manner as above except that each of the comparison compounds shown in Table 4 below were used in place of Compounds I-3, I-4, I-7, and I-13, and the sensitivity thereof is also shown in Table 4.

TABLE 4

| Example No. | Photopolymerization Initiator | Maximum Step No. of Step Wedge |
|---|---|---|
| Example 7 | I-3 | 13 |
| Example 8 | I-4 | 14 |
| Example 9 | I-7 | 14 |
| Example 10 | I-13 | 13 |
| Comparison Example 11 | 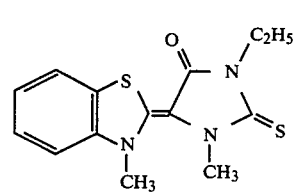 | 0 |
| Comparison Example 12 | 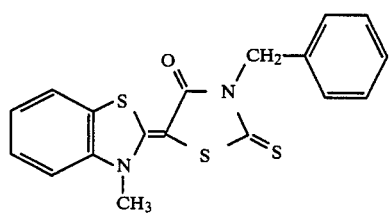 | 4 |
| Comparison Example 13 | 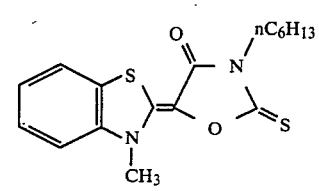 | 7 |

TABLE 4-continued

| Example No. | Photopolymerization Initiator | Maximum Step No. of Step Wedge |
|---|---|---|
| Comparison Example 14 | [benzothiazole with N-CH3, =C(C(=O)-O-N=benzoyl)] structure | 2 |
| Comparison Example 15 | [benzothiazole with N-CH3, =CH-C(=O)-phenyl] structure | 8 |
| Comparison Example 16 | [benzothiazole with N-CH3, =C(C(=O)-phenyl)2] structure | 10 |
| Comparison Example 17 | [benzothiazole with N-CH3, =C(indane-1,3-dione)] structure | 10 |
| Comparison Example 18 | [benzothiazole with N-CH3, =C(CN)(CO2C2H5)] structure | 1 |
| Comparison Example 19 | [benzothiazole with N-CH3, =C(C(=O)-O-N=C-phenyl)] isoxazole structure | 3 |
| Comparison Example 20 | [benzothiazole with N-CH3, =C(C(=O)-N-phenyl)2] structure | 3 |

From the results shown in Table 4, it can be seen that the sensitivities of the samples of this invention in Examples 7 to 10 using the photopolymerization initiators of this invention are superior to the samples in Comparison Samples 11 to 20 using the conventional photopolymerization initiators.

EXAMPLE 11 AND COMPARISON EXAMPLES 21 TO 23

This example shows the excellent effect of a preferred embodiment of this invention using the photopolymerization initiator of this invention shown by general formula (I) above and a combination of the aforesaid specific active agents, i.e., one of the component group (a) and one of the component group (b) described hereinbefore. In addition, Comparison Examples 21 and 22 are expressed as "comparison" for the sample of using the photopolymerization initiator together with the above-described combination and are still the examples of this invention since they also contain the photopolymerization initiator of this invention.

By following the same procedure as in Examples 4 to 6 except that Component (a) and Component (b) shown below were used in place of the active agent in the amounts shown in Table 5 below, a light-sensitive plate was prepared and then exposed and developed as in Examples 4 to 6.

The maximum step number of the step wedge corresponding to the appeared image is shown in Table 5 below as the sensitivity of the sample.

Component (a)

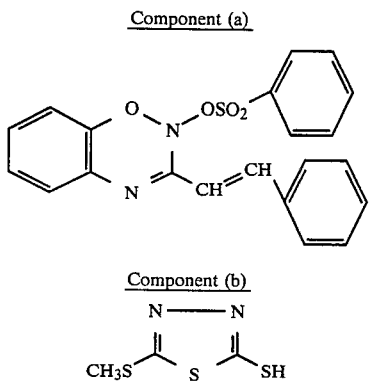

Component (b)

N———N
   ‖    ‖
CH₃S   S   SH

Also, comparison samples were prepared by following the same procedure as above except that one of the photopolymerization initiator, Component (a), and Component (b) was omitted in each case and exposed and developed as above. The sensitivity of the samples are also shown in Table 5 below.

TABLE 5

| Example No. | Amount of Initiator (mole %) | Amount of Component (a) (mole %) | Amount of Component (b) (mole %) | Maximum Step No. of Step Wedge |
|---|---|---|---|---|
| Example 11 | 5 | 5 | 2 | 14 |
| Comparison Example 21* | 5 | 5 | 0 | 12 |
| Comparison Example 22* | 5 | 0 | 2 | 7 |
| Comparison Example 23 | 0 | 5 | 2 | 3 |

(Note):
In the above table, the sample of Comparison Example 21 is same as the sample of Example 6 described above and the sample of Comparison Example 22 is still an example of this invention as described above.

From the results shown in Table 5, it can be seen that the sample of this invention containing the photopolymerization initiator together with the combination of Component (a) and Component (b) (i.e., one of the component group (a) and one of the component group (b) described hereinabove) has a greatly high sensitivity as compared with other sample.

EXAMPLE 12 AND COMPARISON EXAMPLES 24 TO 26

This example also shows the excellent effect of a preferred embodiment as in Example 11 as compared with other examples of this invention (shown as Comparison Examples 24 and 25 in the present invention) and Comparison Example 26 containing no photopolymerization initiator of this invention shown by formula (I).

By following the same procedure as Example 11 except that following Component (a) and Component (b) were used as a combination of the specific active agents, i.e., one of the component group (a) and one of Component (b) described above, a light-sensitive plate was prepared and exposed and developed as in Example 11. The maximum step number of the step wedge corresponding to the appeared image is in Table 6 below.

Component (a)

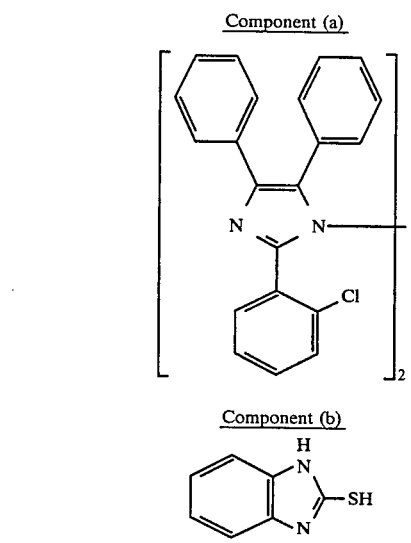

Component (b)

benzothiazole-SH

TABLE 6

| Example No. | Amount of Initiator (mole %) | Amount of Component (a) (mole %) | Amount of Component (b) (mole %) | Maximum Step No. of Step Wedge |
|---|---|---|---|---|
| Example 12 | 5 | 5 | 2 | 13 |
| Comparison Example 24* | 5 | 5 | 0 | 11 |
| Comparison Example 25* | 5 | 0 | 2 | 7 |
| Comparison Example 26 | 0 | 5 | 2 | 4 |

*Comparison Examples 24 and 25 are also examples of this invention as described above.

As shown in the above table, it can be seen that the sample of Example 12 has a very high sensitivity as compared with the samples of other examples, in particular, as compared with the sample outside the scope of this invention.

EXAMPLES 13 TO 16 AND COMPARISON EXAMPLE 27

By following the same procedure as in Example 11 except that Compound I-3 shown hereinabove was used in an amount of 2 mole% as the photopolymerization initiator of this invention shown by formula (I), Component (a) shown below was used in an amount of 5 mole% as one of the component group (a) shown above, the each of the compounds shown in Table 7 below was used in an amount of 2 mole% as one of the component group (b) shown above, each light-sensitive plates was prepared and exposed and developed as in Example 11. The maximum step number of the step wedge corresponding to the appeared image is shown in Table 7 as the sensitivity thereof.

Component (a)

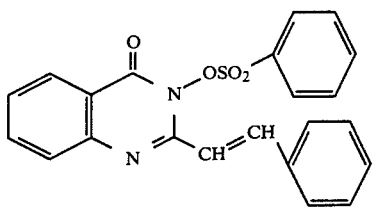

TABLE 7

| Example No. | Component (b) | Maximum Step No. of Step Wedge |
|---|---|---|
| Example 13 | phenyl-NHCH₂CO₂H | 11 |
| Example 14 | benzothiazole-SH | 10 |
| Example 15 | 4,4-dimethylcyclohexane-1,3-dione | 9 |
| Example 16 | 1,3-diethyl-2-thiobarbituric acid | 9 |
| Comparison | None | 7 |

TABLE 7-continued

| Example No. | Component (b) | Maximum Step No. of Step Wedge |
|---|---|---|
| Example 27 | | |

(Note)
In Table 7, Comparison Example 27 is still an example of this invention.

As shown in the results of Tables 5, 6 and 7, it can be seen that the samples of Examples 13 to 16 using the photopolymerization initiator together with the combination of the specific active agents have very high sensitivities as compared with the sample using the initiator together with one of the active agents.

EXAMPLES 17 TO 19 AND COMPARISON EXAMPLES 28 TO 36

By following the same procedure as in Examples 1 to 3 except that each of compounds II-4, II-11, and II-17 described hereinbefore were used in an amount of 5 mole% to each monomer as the photopolymerization initiator of this invention shown by general formula (II) above in place of the photopolymerization initiator shown by Formula (I), each light-sensitive material was prepared and exposed and developed as in Examples 1 to 3 except that the exposure time was 30 seconds. The maximum number of the step wedge corresponding to the appeared image is shown in Table 8 as the sensitivity of the sample.

TABLE 8

| Example | Photopolymerization Initiator | Maximum Step No. of Step Wedge |
|---|---|---|
| 17 | Compound II-4 | 10 |
| 18 | Compound II-11 | 9 |
| 19 | Compound II-17 | 10 |

Also, for comparison, by following the same procedure as above using each of the comparison compounds shown in Table 9 below was used in an amount of 5 mole% to monomer in place of the photopolymerization initiator of this invention shown by formula (II), each comparison sample was prepared and exposed and developed as above. The sensitivities thereof are shown in Table 9.

TABLE 9

| Comparison Example | Photopolymerization Initiator | Maximum Step No. of Step Wedge |
|---|---|---|
| 28 | (structure with triphenylamine, CH=, N-C₂H₅, N-CH₃, S) | 0 |
| 29 | (structure with triphenylamine, CH=, N-nC₆H₁₃, S, S) | 0 |

TABLE 9-continued
| Comparison Example | Photopolymerization Initiator | Maximum Step No. of Step Wedge |
|---|---|---|
| 30 | 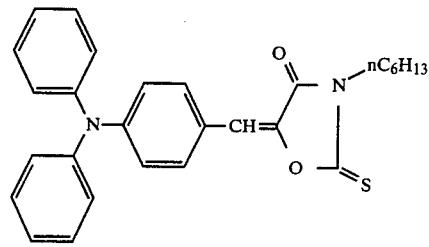 | 4 |
| 31 | 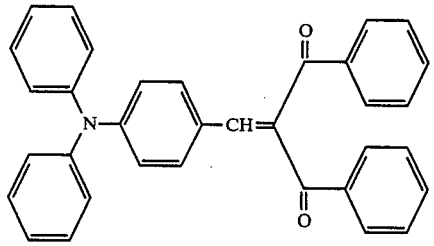 | 0 |
| 32 | 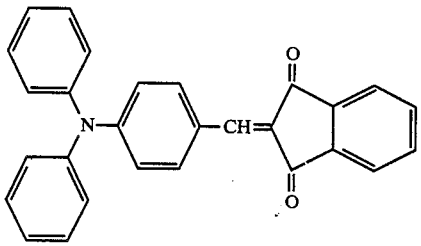 | 0 |
| 33 | 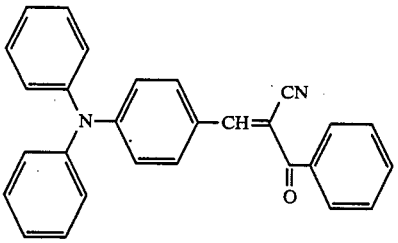 | 0 |
| 34 | 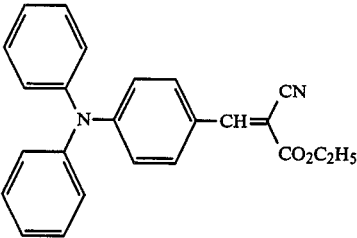 | 2 |

TABLE 9-continued

| Comparison Example | Photopolymerization Initiator | Maximum Step No. of Step Wedge |
|---|---|---|
| 35 | (structure: triphenylamine-CH=C(C(=O)-O-N=) with phenyl group) | 0 |
| 36 | (structure: triphenylamine-CH=C with two C(=O)-N(phenyl) groups forming a ring) | 2 |

As shown in Table 8 and Table 9, it can be seen that the samples of this invention using the photopolymerization initiators shown by formula (II) have higher sensitivities than those of the samples in Comparison Examples 28 to 36.

EXAMPLES 20 TO 22 AND COMPARISON EXAMPLE 37

By following the same procedure as in Example 19 except that each of the active agents shown in Table 10 below was used in an amount of 5 mole% to monomer together with the photopolymerization initiator (Compound II-17), each light-sensitive material was prepared and exposed for 15 seconds and developed by the same manner as in Example 19. The maximum number of the step wedge corresponding to the appeared image is shown in Table 10. Also, for comparison, by following the same procedure above except that the active agent was not used, a comparison sample was prepared as Comparison Example 37 and the sensitivity thereof is also shown in Table 10. In addition, the sample of the comparison example contains the initiator of this invention shown by formula (II) and hence is still a sample of an example of this invention.

TABLE 10

| Example No. | Active Agent | Maximum Step No. of Step Wedge |
|---|---|---|
| Example 20 | (triazine with three CCl₃ groups) | 9 |
| Example 21 | (CH₃S-phenyl-C(=O)-C(OCH₃)₂-N-morpholine) | 8 |
| Example 22 | (benzoyl-N(OSO₂-phenyl)-C=N-fused ring with CH=CH-phenyl) | 11 |
| Comparative Example 37 | None | 7 |

As shown in Table 10 above, it can be seen that the samples of Examples 20 to 22 containing the photopolymerization initiator of this invention shown by formula (II) above show higher sensitivity than that of the sample containing the initiator alone.

EXAMPLES 23 TO 25

By following the same procedure as Examples 17 to 19 described above except that each of Compound II-3, Compound II-14, and Compound II-15 described hereinbefore was used in an amount of 5 mole% to monomer as the photopolymerization initiator shown by formula (II) and 2-styryl-3-phenylsulfonyloxy-4(3H)quinazolinone was used in an amount of 5 mole% to monomer as the active agent, each light-sensitive plate was prepared.

The step wedge as used in the above-described examples was place on each light-sensitive plate and further Fuji Filter SC40 (a filter transmitting light of wavelengths of 400 nm or more, made by Fuji Photo Film Co., Ltd.) or Fuji Filter BPB50 (a filter transmitting light of wavelengths of about 500 nm, a half value width of 45 nm, made by Fuji Photo Film Co., Ltd.) was placed thereon and the light-sensitive plate was exposed for 20 seconds by the same manner as Examples 17 to 19 and developed as in these examples.

The maximum step number of the step wedge corresponding to the appeared image is shown in Table 11.

TABLE 11

| Example | Photopolymerization Initiator | Filter | Maximum Step No. of Step Wedge |
|---|---|---|---|
| 23 | 3 | SC40 | 8 |
| 24 | 14 | " | 9 |
| 25 | 15 | " | 10 |
| 23 | 3 | BPB50 | 7 |
| 24 | 14 | " | 7 |
| 25 | 15 | " | 7 |

From the results shown in Table 11, it can be seen that the samples containing the photopolymerization initiators of this invention shown by formula (II) shown high sensitivity for visible light of wavelengths of 400 nm or more and also for light of wavelengths of about 500 nm.

EXAMPLE 26 AND COMPARISON EXAMPLES 38 TO 40

This invention shows the excellent effects of a preferred embodiment of this invention using the photopolymerization initiator of this invention shown by general formula (II) above and a combination of the above-described specific active agents, i.e., one of the component group (a) and the component group (b) described hereinbefore. In addition, Comparison Examples 38 and 39 are expressed as "Comparison" for the sample of using the initiator together with the aforesaid combination but are still examples of this invention since they also contain of initiator of this invention.

By following the same procedure as Examples 17 to 19 except that Compound II-20 described hereinbefore was used as the photopolymerization initiator of this invention shown by general formula (II), and Component (a) and Component (b) shown below were used as a combination of the specific active agents, i.e., one of the active group (a) and one of the active group (b) described hereinbefore, a light-sensitive material was prepared, exposed for 4 seconds and developed as in the aforesaid examples. The maximum step number of the step wedge corresponding to the appeared image is shown in Table 12 as the sensitivity thereof.

Also, for comparison, by following the same procedure while omitting one of the above-described initiator, Component (a), and Component (b), each comparison sample was prepared, exposed and developed as above. The sensitivities thereof are also shown in Table 12.

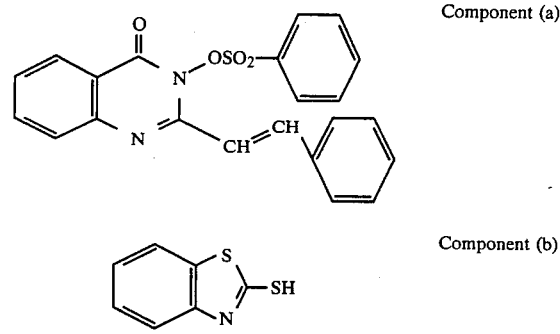

TABLE 12

| Example No. | Amount of Initiator (mole %) | Amount of Component (a) (mole %) | Amount of Component (b) (mole %) | Maximum Step No. of Step Wedge |
|---|---|---|---|---|
| Example 26 | 5 | 5 | 2 | 10 |
| Comparison Example 38* | 5 | 5 | 0 | 7 |
| Comparison Example 39* | 5 | 0 | 2 | 5 |
| Comparison Example 40 | 0 | 5 | 2 | 4 |

*Comparison Examples 38 and 39 are also examples of this invention.

As shown in the table, it can be seen that the use of the photopolymerization initiator shown by formula (II) together with the combination of the specific active agents gives very high sensitivity as compared with the comparison samples.

EXAMPLE 27 AND COMPARISON EXAMPLES 41 TO 43

By following Example 26 described above except that Compound II-16 was used as the photopolymerization initiator of this invention shown by formula (II) and Component (a) and Component (b) shown below were used as the combination of the specific active agents, a light-sensitive material was prepared, exposed and developed as in Example 26.

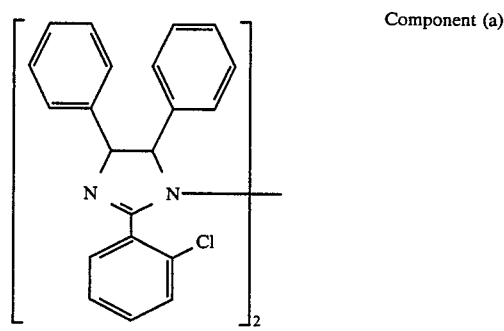

-continued

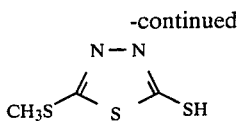

Component (b)

TABLE 13

| Example No. | Amount of Initiator (mole %) | Amount of Component (a) (mole %) | Amount of Component (b) (mole %) | Maximum Step No. of Step Wedge |
|---|---|---|---|---|
| Example 27 | 5 | 5 | 2 | 10 |
| Comparison Example 41* | 5 | 5 | 0 | 8 |
| Comparison Example 42* | 5 | 0 | 2 | 7 |
| Comparison Example 43 | 0 | 5 | 2 | 5 |

*Comparison Examples 41 and 42 are also examples of this invention since they contain the photopolymerization initiator of this invention.

As shown in the above table, it has been seen that the sample of Example 27 containing the photopolymerization initiator shown by formula (II) together with the combination of the specific active agents shown above has very high sensitivity as compared with the comparison samples.

EXAMPLES 28 TO 31 AND COMPARISON EXAMPLE 44

By following the same procedure as in Example 26 except that compound II-7 was used in an amount of 2 mole% to monomer as the photopolymerization initiator of this invention by formula (II), and a combination of Component (a) shown below in an amount of 5 mole% and Compound (b) shown in Table 14 in an amount of 2 mole% was used as the combination of the specific active agents in this invention, a light-sensitive material was prepared, exposed and developed as in Example 26. The maximum step number of the step wedge corresponding to the appeared image is shown in Table 14 as the sensitivity thereof.

Component (a)

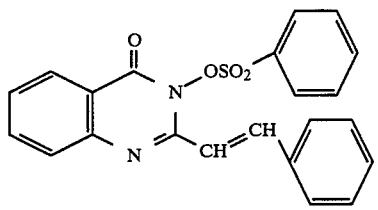

Also, a comparison sample was prepared by following the same procedure as above except that Component (b) was not used. The comparison sample was exposed and developed as above. The sensitivity of the sample is also shown in Table 14.

TABLE 14

| Example No. | Component (b) | Maximum Step No. of Step Wedge |
|---|---|---|
| Example 28 | ⌬—NHCH₂CO₂H | 10 |
| Example 29 | (benzothiazole-SH) | 9 |
| Example 30 | (dimethylcyclohexanedione) | 8 |
| Example 31 | (diethyl thiobarbiturate) | 8 |
| Comparison Example 44 | None | 6 |

(Note):
In Table 14, the sample of Comparison Example 44 is also an example of this invention since it contains the photopolymerization initiator of this invention.

As shown in above Tables 12, 13 and 14, it can be seen that the samples of this invention containing the photopolymerization initiator of this invention shown by formula (II) together with the combination of the specific active agents show very high sensitivity as compared with the sample of Comparison Example 44.

EXAMPLES 32 and 33

By following the same procedure as in Example 26, a light-sensitive material was prepared. The step wedge used in the aforesaid example was placed in the light-sensitive material and also Fuji Filter SC40 (a filter transmitting light of wavelengths of 400 nm or more, made by Fuji Photo Film Co., Ltd.) or Fuji Filter BPB50 (a filter transmitting light of wavelengths of about 500 nm, a half value width of 45 nm, made by Fuji Photo Film Co., Ltd.) was placed thereon. Then, the light-sensitive plate was exposed for 20 seconds and developed as in Example 26. The maximum step number of the step wedge corresponding to the appeared image is shown in Table 15 below.

TABLE 15

| Example | Filter | Maximum Step Wedge No. |
|---|---|---|
| 32 | SC40 | 10 |
| 33 | BPB50 | 7 |

As clear from the results shown in Table 15, it can be seen that the samples of this invention containing the photopolymerization initiator together with the combination of the specific active agents have a very high sensitivity for visible light of wavelengths of 400 nm or more, and for light of wavelengths of about 500 nm.

While the invention has been described in detail and with reference to specific embodiments thereof, it will be apparent to one skilled in the art that various changes and modifications can be made therein without departing from the spirit and scope thereof.

What is claimed is:

1. A photopolymerizable composition containing an addition polymerizable compound having at least one ethylenically unsaturated double bond and a photopolymerization initiator, wherein the photopolymerizable composition contains at least one compound represented by following general formula (I) or (II) as the photopolymerization initiator:

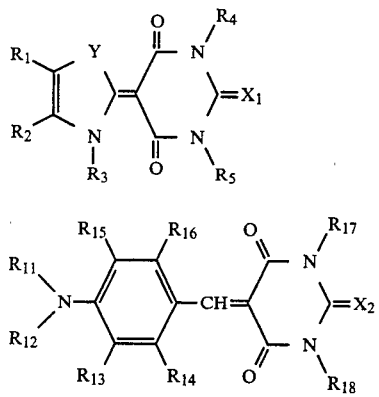

wherein, $R_1$, $R_2$, $R_3$, $R_4$, and $R_5$ each represents a hydrogen atom, an alkyl group, a substituted alkyl group, an aryl group, a substituted aryl group, an allyl group or a substituted allyl group, said $R_1$ and $R_2$ may combine with each other to form a ring together with the carbon atoms to which they are bonded; Y represents —O—, —S—, —Se—, —C(CH$_3$)$_2$— or —CH=CH—; $X_1$ represents an oxygen atom or a sulfur atom; $R_{11}$, $R_{12}$, $R_{17}$, and $R_{18}$ each represents a hydrogen atom, an alkyl group, a substituted alkyl group, an aryl group, a substituted aryl group, an allyl group, or a substituted allyl group; $R_{13}$, $R_{14}$, $R_{15}$, and $R_{16}$ each represents a hydrogen atom, an alkyl group, a substituted alkyl group, an aryl group, a substituted aryl group, a halogen atom, a carboalkoxy group, or an alkoxy group; said $R_{11}$ and $R_{15}$, said $R_{12}$ and $R_{13}$, said $R_{15}$ and $R_{16}$, and said $R_{13}$ and $R_{14}$ each may combine with each other to form a ring together with the carbon atoms to which they are bonded; and $X_2$ represents an oxygen atom or a sulfur atom.

2. The photopolymerizable composition as claimed in claim 1, wherein said photopolymerizable composition further contains an active agent.

3. The photopolymerizable composition as claimed in claim 2, wherein said active agent is selected from a carbonyl compound, a sulfonyloxime compound, an acyloxime compound, a hexaarylbiimidazole compound, a halogenated compound, an amino compound, an amino acid, a sulfur compound, and a peroxide.

4. The photopolymerizable composition as claimed in claim 2, wherein the active agent is composed of a combination of at least one of component group (a) consisting of a hexaarylbiimidazole and a sulfonyloxime compound represented by general formula (VIII):

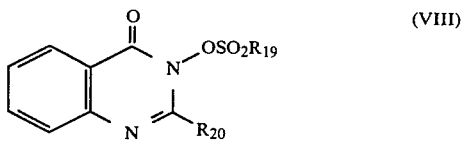

wherein $R_{19}$ and $R_{20}$ each represents an alkyl group, substituted alkyl group, an aryl group, a substituted aryl group, an alkenyl group, or a substituted alkenyl group, and at least one of the component group (b) consisting of an α,β-dicarbonyl compound, an N-phenylglycine, and a thiol compound represented by general formula (IX)

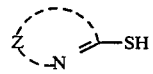

wherein Z represents a non-metallic group necessary for forming a heterocyclic ring.

5. The photopolymerizable composition as claimed in claim 2, wherein said active agent is 2,6-di(trichloromethyl)-4-(p-methoxyphenyl)-1,3,5-triazine, 2,4,6-tri(trichloromethyl)-1,3,5-triazine, 2-trichloromethyl-5-(p-methoxystyryl)-1,3,4-oxadiazole, anthraquinone-1-sulfonyl chloride, or 2,2,2-trichloroacetophenone.

6. The photopolymerizable composition as claimed in claim 1, wherein said photopolymerization initiator is used in an amount of 0.01 to 50 parts by weight based on 100 parts by weight of the polymerizable compound having an ethylenically unsaturated bond.

7. The photopolymerizable composition as claimed in claim 6, wherein the photopolymerization initiator is used in an amount of 0.1 to 10 parts by weight based on 100 parts by weight of the polymerizable compound having an ethylenically unsaturated bond.

8. The photopolymerizable composition as claimed in claim 2, wherein said active agent is used in an amount of 100 parts by weight or less based on 100 parts by weight of the polymerizable compound having an ethylenically unsaturated bond.

9. The photopolymerizable composition as claimed in claim 4, wherein the component (a) and component (b) are used in an amount of 0.01 to 50 parts by weight based on 100 parts by weight of the polymerizable compound having an ethylenically unsaturated bond, respectively.

10. The photopolymerizable composition as claimed in claim 9, wherein the component (a) and component (b) are used in an amount of 0.1 to 10 parts by weight based on 100 parts by weight of the polymerizable compound having an ethylenically unsaturated bond, respectively.

* * * * *